(12) United States Patent
Lin

(10) Patent No.: US 7,537,843 B2
(45) Date of Patent: May 26, 2009

(54) EMISSION MATERIAL AND ORGANIC ELECTROLUMINESCENT DEVICE USING THE SAME

(75) Inventor: Cheng-Hung Lin, Hemei Township, Changhua County (TW)

(73) Assignee: Au Optronics Corp., Hsin-Chu (TW)

( * ) Notice: Subject to any disclaimer, the term of this patent is extended or adjusted under 35 U.S.C. 154(b) by 607 days.

(21) Appl. No.: 11/192,050

(22) Filed: Jul. 29, 2005

(65) Prior Publication Data
US 2006/0240282 A1    Oct. 26, 2006

(30) Foreign Application Priority Data
Apr. 21, 2005    (TW) ............................... 94112790 A

(51) Int. Cl.
*H01L 51/54*   (2006.01)
*C09K 11/06*   (2006.01)

(52) U.S. Cl. ..................... 428/690; 428/917; 313/504; 313/506; 257/E51.044; 546/4; 548/101; 548/108

(58) Field of Classification Search ................... None
See application file for complete search history.

(56) References Cited

U.S. PATENT DOCUMENTS

| | | |
|---|---|---|
| 2002/0024293 A1 | 2/2002 | Igarashi et al. |
| 2002/0121638 A1 | 9/2002 | Grushin et al. |
| 2002/0134984 A1 | 9/2002 | Igarashi |
| 2002/0182441 A1 | 12/2002 | Lamansky et al. |
| 2004/0091738 A1 | 5/2004 | Psai et al. |
| 2004/0137267 A1* | 7/2004 | Igarashi et al. .............. 428/690 |
| 2007/0048546 A1* | 3/2007 | Ren ........................... 428/690 |

\* cited by examiner

*Primary Examiner*—Marie R. Yamnitzky
(74) *Attorney, Agent, or Firm*—Rabin & Berdo, PC

(57) ABSTRACT

An organic electroluminescent device (OELD) is provided. The OELD includes a substrate, an anode, a cathode, a hole transport layer, an electron transport layer and an emission layer. The anode and the cathode are disposed on the substrate. The hole transport layer is disposed between the anode and the cathode. The electron transport layer is disposed between the hole transport layer and the cathode. The emission layer is disposed between the hole transport layer and the electron transport layer. The emission layer includes a host and a dopant. The chemical structure of the dopant is shown as the formula [I]:

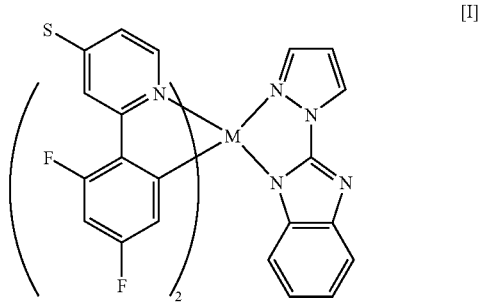

"M" is a metal atom whose atomic weight is greater than 40. "S" is selected from a group consisting of alkyl, alkoxy, haloalkyl, halogen, hydrogen and any other substituents.

8 Claims, 2 Drawing Sheets

EMISSION MATERIAL AND ORGANIC ELECTROLUMINESCENT DEVICE USING THE SAME

This application claims the benefit of Taiwan application Ser. No. 94112790, filed Apr. 21, 2005, the subject matter of which is incorporated herein by reference.

BACKGROUND OF THE INVENTION

1. Field of the Invention

The invention relates in general to an emission material and an organic electroluminescent device (OELD) using the same, and more particularly to a pure blue emission material and an organic electroluminescent device using the same.

2. Description of the Related Art

Conventional organic electroluminescent device (OELD) is a multi-layer stacked structure and includes a substrate, an anode, a cathode, a hole injection layer, a hole transport layer, an electron transport layer, an electron injection layer and an emission layer. The anode, the hole injection layer, the hole transport layer, the emission layer, the electron transport layer, the electron injection layer and the cathode are sequentially disposed on the substrate from bottom to up. The emission layer includes a host and dopant system, that is, the host is mixed with a small amount of dopant. As for how to determine whether the host and dopant system is a fluorescent host and dopant system or a phosphorescent host and dopant system is disclosed below.

When a voltage is applied to the cathode and the anode, the electron will pass through the electron injection layer and the electron transport layer to be injected into the emission layer from the cathode, and the hole will pass through the hole injection layer and the hole transport layer to be injected into the emission layer from the anode. After the electron and the hole are combined in the emission layer, the host will be excited to the exciton state from the ground state. Since the host is unstable at the exciton state, the host would return to the ground state from the exciton state and transfer energy to the dopant at the same time.

When the dopant receives the energy and is accordingly excited to the exciton state from the ground state, the dopant would generate both singlet excitons and triplet excitons. Regardless of the dopant being fluorescent or phosphorescent, the ratio of the probability of forming the triplet exciton to the probability of forming the singlet exciton is approximately 3:1 due to the distribution ratio of the electron spin state.

Both the singlet exciton and the triplet exciton return to the stable ground state by releasing photons, enabling the OELD to be electroluminescent. In the fluorescent host and dopant system, only the light emitted when the singlet exciton returns to the ground state is visible fluorescence. In the phosphorescent host and dopant system, the light emitted when the triplet exciton returns to the ground state is visible phosphorescence, so is the light emitted when the singlet exciton returns to the ground state visible phosphorescence after the conversion of internal system crossing (ISC).

Since the blue phosphorescent material has not achieved the standards of the fluorescent material in terms of color purity and lifespan, the red and green phosphorescent materials are mainly applied to the OELD according to their characteristics and lifespan have achieved commercializing standards.

The color of the conventional blue phosphorescent material iridium(III) bis(4,6-di- fluolophenyl)-pyridinato-N,C2') picolinate (Flrpic) is not blue enough. As for other conventional blue phosphorescent materials, some materials are bluer when dissolved in a solution but are not blue enough when disposed in a device.

SUMMARY OF THE INVENTION

It is therefore the object of the invention to provide an emission material and an organic electroluminescent device (OELD) using the same. The emission material according to the invention is the featured by an easily formed structure and a bluer color, hence the emission material according to the invention is bluer than the conventional blue phosphorescent material. Furthermore, the luminous efficiency of the device using the emission material according to the invention can achieve as high as 6 cd/A or even above.

According to an object of the invention, an emission material is provided. The chemical structure of the emission material is shown as formula [I]:

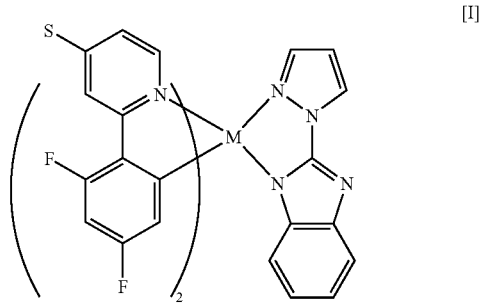

In the above formula, "M" is a metal atom whose atomic weight is greater than 40, while "S" is selected from a group consisting of alkyl, alkoxy, haloalkyl, halogen, hydrogen and any other substituents.

Furthermore, "M" is selected from a group consisting of osmium (Os), ruthenium (Ru), iridium (Ir), platinum (Pt), rhenium (Re), thallium (Tl), palladium (Pb) and rhodium (Rh), while "S" can be methoxyl. Besides, the abovementioned emission material serves as a blue emission material such as a blue phosphorescent dopant, and the abovementioned emission material is an octahedral structure. Moreover, the abovementioned emission material emits a light whose wavelength ranges from 400 nm to 500 nm. For example, the wavelength of the light provided by the emission material equals 464 nm.

According to another object of the invention, an organic electroluminescent device (OELD) is provided. The OELD includes a substrate, an anode, a cathode, a hole transport layer, an electron transport layer and an emission layer. The anode and the cathode are disposed on the substrate. The hole transport layer is disposed between the anode and the cathode. The electron transport layer is disposed between the hole transport layer and the cathode. The emission layer is disposed between the hole transport layer and the electron transport layer. The emission layer includes a host and a dopant. The chemical structure of the dopant is shown as the formula [I]:

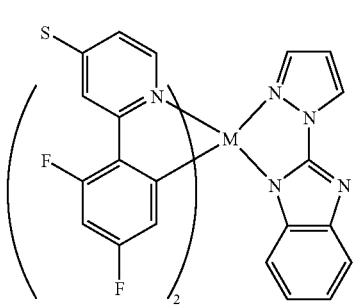

[I]

In the above formula, "M" is a metal atom whose atomic weight is greater than 40. "S" is selected from a group consisting of alkyl, alkoxy, haloalkyl, halogen, hydrogen and any other substituents.

Furthermore, "M" is selected from a group consisting of osmium (Os), ruthenium (Ru), iridium (Ir), platinum (Pt), rhenium (Re), thallium (Tl), palladium (Pb) and rhodium (Rh), while "S" can be methoxyl. Besides, the abovementioned dopant serves as a blue dopant, and the abovementioned dopant is an octahedral structure. Moreover, the abovementioned dopant emits a light whose wavelength ranges from 400 nm to 500 nm. For example, the wavelength of the light provided by the dopant equals 464 nm. The concentration of the abovementioned dopant in the emission layer ranges from 1 wt % to 20 wt %.

The abovementioned OELD further includes a hole injection layer disposed between the hole transport layer and the anode. Furthermore, the abovementioned OELD further includes an electron injection layer disposed between the electron transport layer and the cathode. Besides, the abovementioned OELD further includes a hole blocking layer disposed between the electron transport layer and the emission layer.

Other objects, features, and advantages of the invention will become apparent from the following detailed description of the preferred but non-limiting embodiments. The following description is made with reference to the accompanying drawings.

DETAILED DESCRIPTION OF THE INVENTION

FIRST EMBODIMENT

Figure 1:
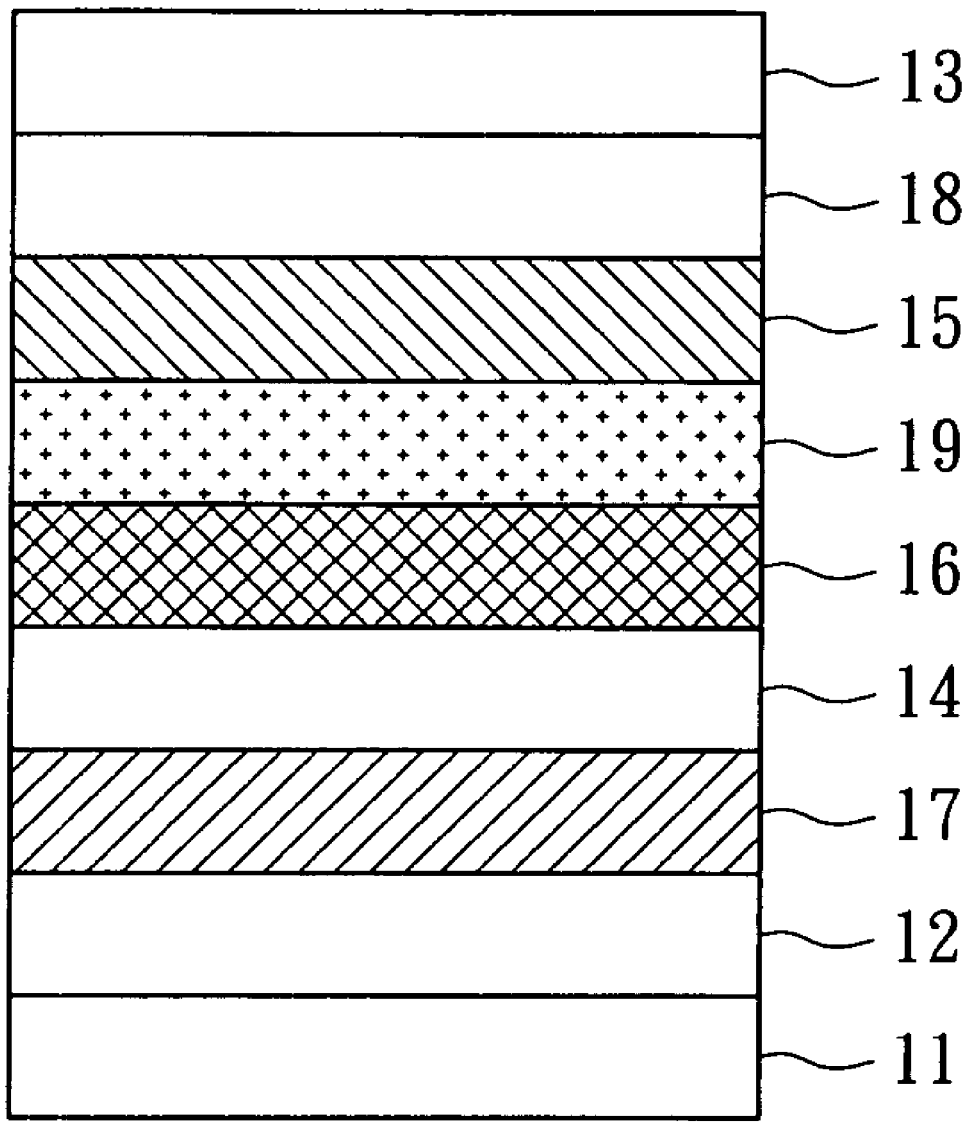
FIG. 1 is a structural diagram of an organic electroluminescent device (OELD) according to a second embodiment of the invention.

The first embodiment of the invention provides a emission material whose chemical structure is shown as formula [I]:

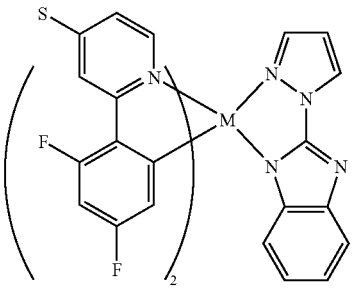

[I]

In the above formula, "M" is a metal atom whose atomic weight is greater than 40, while "S" is selected from a group consisting of alkyl, alkoxy, haloalkyl, halogen, hydrogen and any other substituents.

Furthermore, "M" is selected from a group consisting of osmium (Os), ruthenium (Ru), iridium (Ir), platinum (Pt), rhenium (Re), thallium (Tl), palladium (Pb) and rhodium (Rh), while "S" can be methoxyl.

Besides, the abovementioned emission material is an octahedral structure, and the abovementioned emission material emits a light whose wavelength ranges from 400 nm to 500 nm, for example, 464 nm. So that, there is an emission from the emission material of the present embodiment comprising blue phosphorescence. Moreover, the abovementioned emission material can serves as a blue emission material such as a blue phosphorescent dopant. The emission material of the present embodiment can also be made into a phosphorescent material or a fluorescent material with other colors.

In the present embodiment, the central metal of the emission material is made of Ir mainly with the Fppy ligand and a nitrogen-containing heterocyclic ring sub-ligand further being added to form an emission material with an octahedral structure. The chemical structure of the emission material is shown as [II] and [III]:

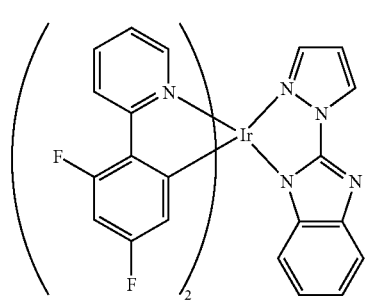

[II]

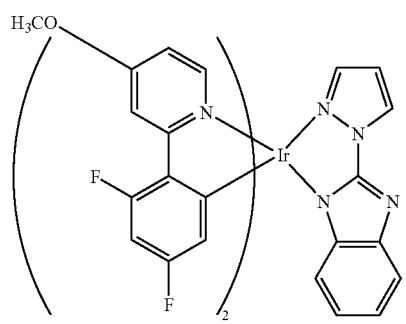

[III]

The manufacturing of the emission material disclosed in the present embodiment is exemplified by the manufacturing process of the emission material whose chemical structure is shown as [II].

The manufacturing process of the emission material whose chemical structure is shown as [II] begins at step (a), pyrazol-benzimidazole is synthesized and is denoted as compound 4 here. The synthetic reaction of the compound 4 is shown below:

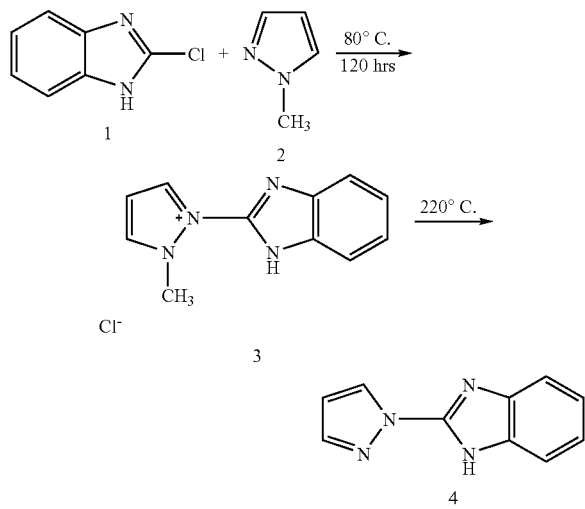

In step (a), one equivalent of 2-chlorobenzimidazole (compound 1) and three equivalents of N-methylpyrazole (compound 2) are heated to 80° C. at a high-pressure sealed tube with the reaction being lasted for 120 hours to form a compound 3. Next, the compound 3 is dissolved in dichloromethane ($CH_2Cl_2$) and then filtered. Afterwards, the filtrate is concentrated, dried, decompressed and heated to 220° C., then pyrazol-benzimidazole (compound 4) is obtained with a yield rate of 50% approximately.

Next, proceed to step (b), the emission material whose chemical structure is shown as [II] is synthesized. The synthetic reaction of the emission material whose chemical structure is shown as [II] is illustrated below:

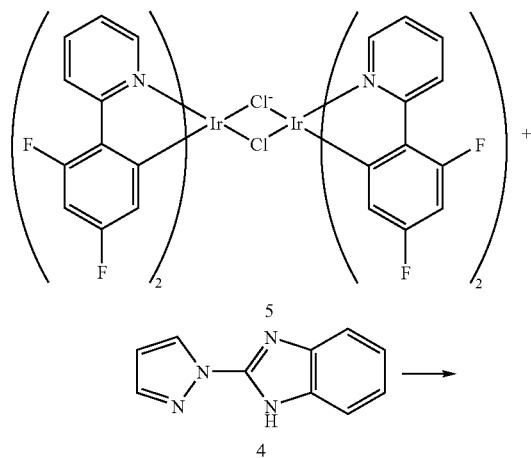

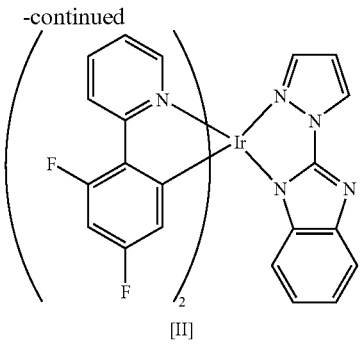

Next, proceed to step (b), one equivalent of pyrazol-benzimidazole (compound 4), half equivalent of $Ir[(Fppy)_2Cl]_2$ (compound 5) and two equivalents of NaOEt are refluxed and heated in $CH_2Cl_2$/MeOH for 16 hours. After 16 hours, the solution is extracted using deionized water (DIW) and $CH_2Cl_2$ for several times and dried. The solution is crystallized to form a yellow solid using $CH_2Cl_2$/hexane. The yellow solid is the emission material whose chemical structure is shown as [II].

The emission material whose chemical structure is shown as [II] is further separated and purified using silicon glue tubular column and then purified through sublimation. Measuring the photoluminescence (PL) spectrum of the compound in a solution, and it can be found that the emission material whose chemical structure is shown as [II] provides a light whose wavelength ranges from 400 nm to 500 nm.

As for the manufacturing process of the emission material whose chemical structure is shown as [III] is elaborated below.

The manufacturing process of the emission material whose chemical structure is shown as [III] begins at step (a), pyrazol-benzimidazole is synthesized and is denoted as compound 4 here. The synthetic reaction of the compound 4 is shown below.

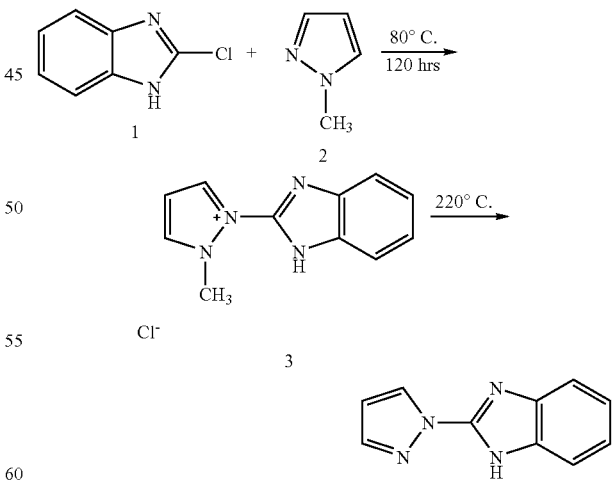

Proceed to step (a), one equivalent of 2-chlorobenzimidazole (compound 1) and three equivalents of N-methylpyrazole (compound 2) are heated to 80° C. at a high-pressure sealed tube with the reaction being lasted for 120 hours to form a compound 3. Next, the compound 3 is dissolved in dichloromethane ($CH_2Cl_2$) and then filtered. Afterwards, the filtrate is concentrated, dried, decompressed and heated to 220° C., then pyrazol-benzimidazole (compound 4) is obtained with a yield rate of 50% approximately.

Next, proceed to step (c), the emission material whose chemical structure is shown as [III] is synthesized. The synthetic reaction of the emission material whose chemical structure is shown as [III] is illustrated below:

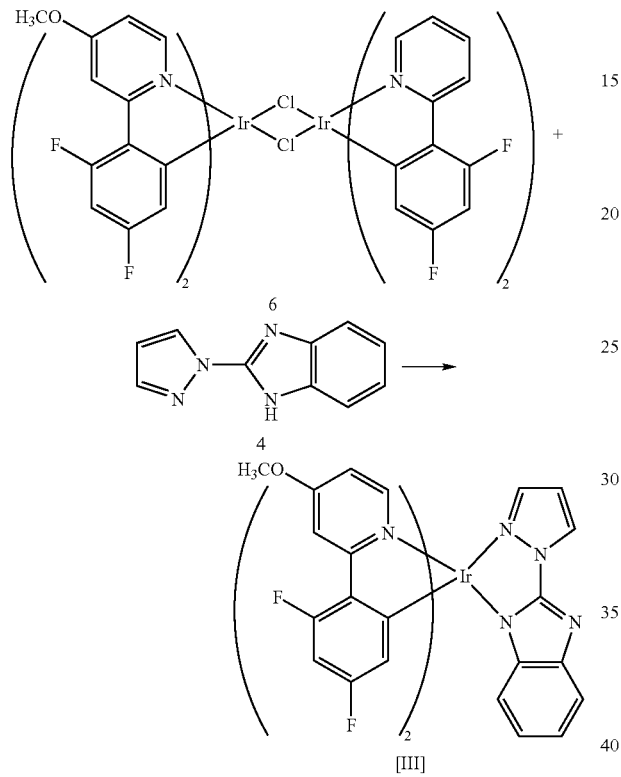

In step (b), one equivalent of pyrazol-benzimidazole (compound 4), half equivalent of compound 6 and two equivalents of NaOEt are refluxed and heated in $CH_2Cl_2$/MeOH for 16 hours. After 16 hours, the solution is extracted using deionized water (DIW) and $CH_2Cl_2$ for several times and dried. The solution is crystallized to form a yellow solid using $CH_2Cl_2$/hexane. The yellow solid is the emission material whose chemical structure is shown as [III].

The emission material whose chemical structure is shown as [III] is further separated and purified using silicon glue tubular column and then purified through sublimation. Measuring the photoluminescence (PL) spectrum of the compound in a solution, and it can be found that the emission material whose chemical structure is shown as [III] provides a light whose wavelength ranges from 400 nm to 500 nm.

SECOND EMBODIMENT

Referring to FIG. 1, a structural diagram of an organic electroluminescent device (OELD) according to a second embodiment of the invention is shown. In the present embodiment, the OELD includes a micromolecular organic light emitting diode (OLED) and a polymer light emitting diode (PLED), is exemplified by an OLED here. However, the technology disclosed in the present embodiment is also applicable to the PLED.

In FIG. 1, The OELD 10 includes a substrate 11, an anode 12, a cathode 13, a hole transport layer 14, an electron transport layer 15 and an emission layer 16. The anode 12 and the cathode 13 are disposed on the substrate 11. The hole transport layer 14 is disposed between the anode 12 and the cathode 13. The electron transport layer 15 is disposed between the hole transport layer 14 and the cathode 13. The emission layer 16 is disposed between the hole transport layer 14 and the electron transport layer 15. The emission layer 16 includes a host and a dopant. The chemical structure of the dopant is shown as formula [I]:

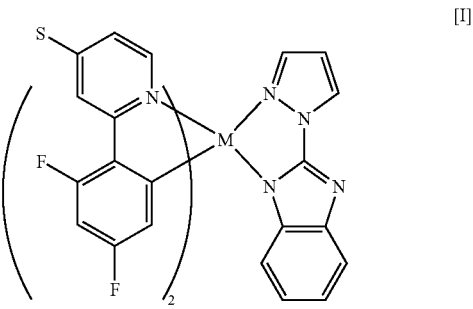

In the above formula, "M" is a metal atom whose atomic weight is greater than 40, while "S" is selected from a group consisting of alkyl, alkoxy, haloalkyl, halogen, hydrogen and any other substituents. Furthermore, "M" is selected from a group consisting of osmium (Os), ruthenium (Ru), iridium (Ir), platinum (Pt), rhenium (Re), thallium (Tl), palladium (Pb) and rhodium (Rh), while "S" can be methoxyl.

In the present embodiment, the central metal of the dopant is made of Ir mainly with the Fppy ligand and a nitrogen-containing heterocyclic ring sub-ligand further being added to form an emission material with an octahedral structure. The chemical structure of the emission material is shown as [II] and [III]:

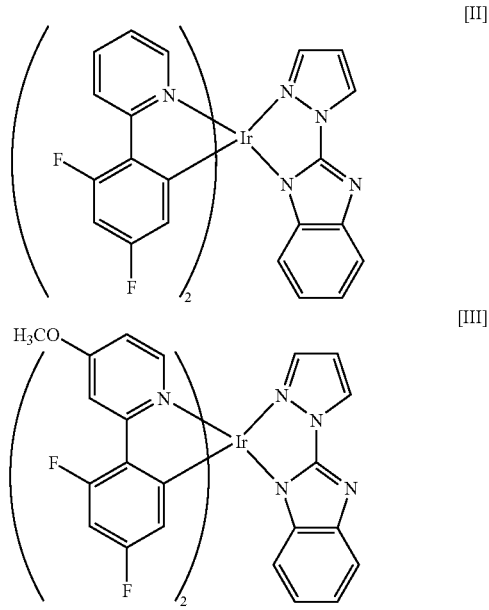

Besides, the abovementioned dopant can serve as a blue dopant. So that, there is an emission from the dopanti of the present embodiment comprising blue phosphorescence. The abovementioned dopant is an octahedral structure. Moreover, the abovementioned dopant emits a light whose wavelength ranges from 400~500 nm. For example, the wavelength of the light provided by the abovementioned dopant equals 464 nm. The concentration of the abovementioned dopant in the emission layer 16 ranges from 1 wt % to 20 wt %.

In the present embodiment, the OELD 10 further includes a hole injection layer 17 disposed between the hole transport layer 14 and the anode 12. The OELD 10 further includes an electron injection layer 18 disposed electron transport layer 15 and the cathode 13. Besides, the OELD 10 further includes a hole blocking layer 19 disposed between the electron transport layer 15 and the emission layer 16.

However, anyone who is skilled in the technology of the present embodiment of the invention will realize that the technology of the present embodiment of the invention is not limited thereto. For example, the anode 12 and the cathode 13 may include a metal, a metal alloy or a transparent conductive material, and at least one of the anode 12 and the cathode 13 must be transparent or semi-transparent. The abovementioned transparent conductive material includes indium tin oxide (ITO), indium zinc oxide (IZO), cadmium tin oxide (CTO), stannim dioxide ($SnO_2$), zinc oxide (ZnO) or other similar transparent metal oxides. The abovementioned metal and metal alloy includes aurum (Au), aluminum (Al), indium (In), magnesium (Mg), calcium (Ca) and so forth.

If the cathode 13 can be a reflective metal only when the anode 12 is transparent or semi-transparent, then the OELD 10 is a bottom emission device and the substrate 11 has to be a transparent or a semi-transparent substrate. If the anode 12 can be a reflective metal only when the cathode 13 is transparent or semi-transparent, then the OELD 10 is a top emission device and the substrate 11 can be a transparent, semi-transparent or non-transparent substrate. When the anode 12 and the cathode 13 are transparent or semi-transparent, the OELD 10 is a dual emission device and the substrate 11 has to be a transparent or a semi-transparent substrate.

The OELD 10 of the present embodiment of the invention can be applied to electronic products such as computer screen, flat TV, monitor screen, vehicle TV, mobile phone, handheld game station, digital camera (DC), digital video (DV), digital audio device, personal digital assistant (PDA), web pad, notebook, handheld computer, laptop computer, table PC, and so forth.

In the manufacturing of the device, the ITO is respectively plated with 406:F4(1500 Å, 2%)/NPB(200 Å)/mCP: IrL(300 Å,10%)/BAlq(400 Å)/LiF(10 Å)/Al to form an OELD. The mCP is N,N'-dicarbozale-1,3-benzene. The NPB is 1, 1-bis[N-(1-naphthyl)-N'-phenylamino]biphenyl-4, 4' diamine. The BAlq is bis (2-methyl-8-quinolinolato) (p-phenylphenolato) aluminum. The ITO, the 406:F4 and the NPB are the anode, the hole injection layer and the hole transport layer, respectively. Furthermore, mCP: IrL is the emission layer, mCP is the host, and IrL denotes the dopant of the present embodiment of the invention. The chemical structure of the dopant is shown as [II] or [III]. Besides, BAlq is the hole blocking layer or the electron transport layer, and the LiF/Al is the compsite cathode. The emission material of the present embodiment of the invention is mixed with the mCP host with the concentration of the emission material is controlled to be under 10 wt %. As for the luminous efficiency of the device, the luminous efficiency of the device can reach as high as 6.2 cd/A under low luminance. As the luminance increases, the luminous efficiency of the device is maintained at 5 cd/A or even above.

On the other hand, the electroluminescence (EL) spectrum of the device also shows that the wavelength of the light provided by the phosphorescent device is mainly 464 nm, and the peak of another longer wavelength which is 490 nm in the photoluminescence (PL) spectrum is now weakened in color when measured in the device. By doing so, the photoluminescence (PL) spectrum of the device according to the present embodiment of the invention becomes even bluer and the CIE can achieve as high as (0.15,0.24).

THIRD EMBODIMENT

Figure 2:
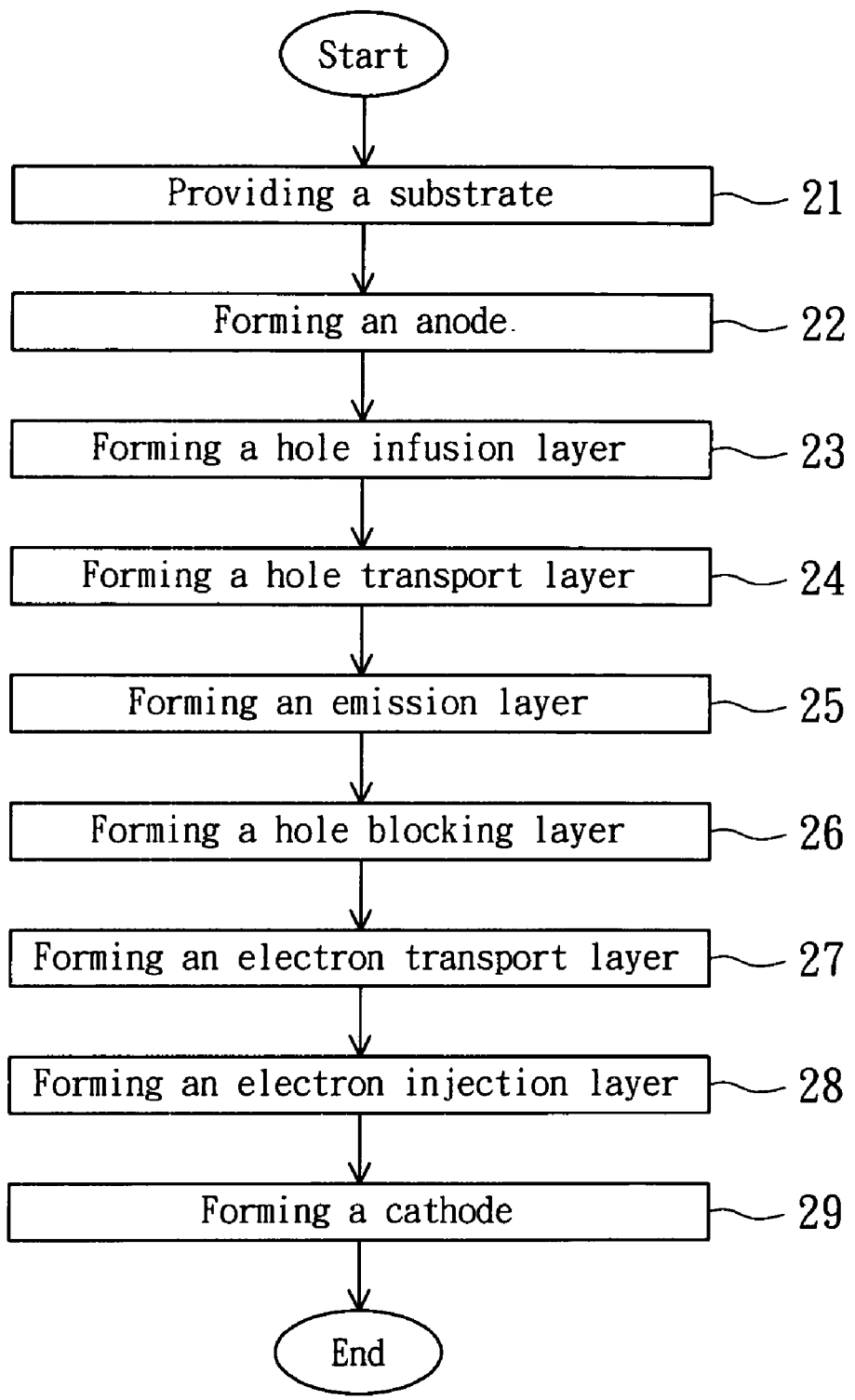
FIG. 2 is a flowchart of the method of manufacturing an OELD according to a third embodiment of the invention.

Referring to FIG. 2, a flowchart of the method of manufacturing an OELD according to a third embodiment of the invention is shown. Referring to FIG. 1 at the same time. At first, the method begins at step 21, a substrate 11 is provided. Next, proceed to step 22, an anode 12 is formed on the substrate 11. Then, proceed to step 23, a hole injection layer 17 is formed on the anode 12. Next, proceed to step 24, a hole transport layer 14 is formed on the hole injection layer 17. Then, proceed to step 25, an emission layer 16 is formed on the hole transport layer 14. The emission layer 16 includes a host and a dopant. The chemical structure of the dopant is shown as he abovementioned formula [I]. Next, proceed to step 26, a hole blocking layer 19 is formed on the emission layer 16. Afterwards, proceed to step 27, an electron transport layer 15 is formed on the hole blocking layer 19. Next, proceed to step 28, an electron injection layer 18 is formed on the electron transport layer 15. Then, proceed to step 29, a cathode 13 is formed on the electron injection layer 18. The OELD 10 is formed.

Despite the emission material of the present embodiment of the invention is exemplified by the dopant, the scope of technology of the present embodiment of the invention is not limited thereto. For example, the emission material of the present embodiment of the invention can also be used as a host to form an emission layer with other dopants.

The emission material and the organic electroluminescent device using the same are disclosed in above embodiments of the invention. The structure of the emission material can be formed easily. The CIE of the device being equal to (0.15, 0.24). Therefore, the emission material of the present embodiment of the invention is bluer than the conventional blue phosphorescent material. Furthermore, the luminous efficiency of the device using the emission material of the present embodiment of the invention can achieve 6 cd/A or even above.

While the invention has been described by way of example and in terms of a preferred embodiment, it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. An organic electroluminescent device (OELD), comprising:
    a substrate;
    an anode and a cathode disposed on the substrate;
    a hole transport layer disposed between the anode and the cathode;
    an electron transport layer disposed between the hole transport layer and the cathode; and
    an emission layer disposed between the hole transport layer and the electron transport layer, wherein the emission layer comprises a host material and a dopant material, and the chemical structure of the dopant material is shown as the formula [I]:

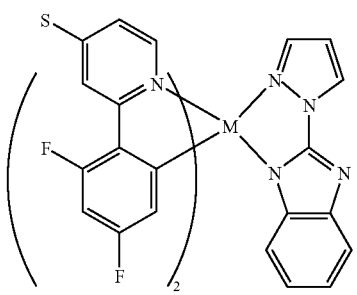 [I]

wherein "M" is a metal whose atomic weight is greater than 40, while "S" is selected from the group consisting of alkyl, alkoxy, haloalkyl, halogen, and hydrogen, wherein the concentration of the dopant material in the emission layer ranges from 1 wt % to 20 wt %.

2. The OELD according to claim 1, wherein "M" is selected from a group consisting of osmium (Os), ruthenium (Ru), iridium (Ir), rhenium (Re), thallium (Tl), and rhodium (Rh).

3. The OELD according to claim 1, wherein "S" is methoxy.

4. The OELD according to claim 1, wherein the dopant material emits a light whose wavelength ranges from 400 nm to 500 nm.

5. The OELD according to claim 4, wherein the wavelength of the light is 464 nm.

6. The OELD according to claim 1, further comprising:
a hole injection layer disposed between the hole transport layer and the anode.

7. The OELD according to claim 1, further comprising:
an electron injection layer disposed between the electron transport layer and the cathode.

8. The OELD according to claim 1, further comprising:
a hole blocking layer disposed between the electron transport layer and the emission layer.

* * * * *